United States Patent
Nakagawa et al.

(10) Patent No.: US 6,455,555 B1
(45) Date of Patent: Sep. 24, 2002

(54) ANTI-HIV INFECTION AGENTS AND METHOD FOR TREATING HIV INFECTION

(75) Inventors: Yoshinori Nakagawa, Okayama (JP); Takehiro Niiyama, Tokyo (JP); Satoshi Tsuboi, Okayama (JP)

(73) Assignee: Kabushiki Kaisha Hayashibara Seibutsu Kagaku Kenkyujo, Okayama (JP)

(*) Notice: Subject to any disclaimer, the term of this patent is extended or adjusted under 35 U.S.C. 154(b) by 0 days.

(21) Appl. No.: 09/868,742
(22) PCT Filed: Dec. 24, 1998
(86) PCT No.: PCT/JP98/05925
§ 371 (c)(1),
(2), (4) Date: Jun. 20, 2001
(87) PCT Pub. No.: WO00/38682
PCT Pub. Date: Jul. 6, 2000
(51) Int. Cl.[7] .................. A61K 31/4418; A61K 31/47; C07D 453/02; C07D 277/04
(52) U.S. Cl. ............. 514/358; 514/311; 514/365; 546/134; 546/152; 546/347; 548/146
(58) Field of Search ................. 514/311, 367, 514/365, 358; 546/134, 152; 548/146

(56) References Cited

U.S. PATENT DOCUMENTS 5,491,151 A * 2/1996 Nakagawa et al. ......... 514/311

FOREIGN PATENT DOCUMENTS

| EP | 0 417 941 A2 | 3/1991 |
| JP | 58 90510 | 5/1983 |
| JP | 03 90025 | 4/1991 |

OTHER PUBLICATIONS

Caplus 117:22546, Matthews et al, Inactivation of Viruses with photoactive compounds, 1992, 18(10, pp. 75–89.*
Brodie et al., "Macrophage Function in Simian AIDS. Killing Defects In Vivo are Independent of Macrophage Infection, Associated with Alterations in Th Phenotype, and Reversible with IFN–γ," *The Journal of Immunology*, 153 (12), 5790–5801 (1994).
Kendall et al., "Preparation of Symmetrical and Unsymmetrical Neocyanines: Structure of the Neocyanines," *J. Chem. Soc.* 690–695 (1948).
Yamamoto et al., "Prognostic Utility of Serum α–N–Acetylgalactosaminidase and Immunosuppression Resulted from Deglycosylation of Serum Gc Protein in Oral Cancer Patients," *Cancer Research*, 57, 295–299 (Jan. 15,1997).
Yamamoto et al., "Activation of Mouse Macrophages by In Vivo and In Vitro Treatment with a Cyanine Dye, Lumin," *J. Photochem. Photobiol. B: Biol.*, 13, 295–306 (1992).
Nakagawa et al., "In Vivo and In Vitro Activation of Macrophages with a Cyanine Photosensitizing Dye, Platonin," *Cancer Immunology Immunotherapy*, 37, 157–162 (1993).

* cited by examiner

*Primary Examiner*—Alan L. Rotman
*Assistant Examiner*—Rita Desai
(74) *Attorney, Agent, or Firm*—Leydig, Voit & Mayer, Ltd.

(57) ABSTRACT

The present invention relates to agents for anti-HIV infection, which contain, as an active ingredient, at least one photosensitizing dye selected from the group consisting of the compounds of the formulae (I) and (II):

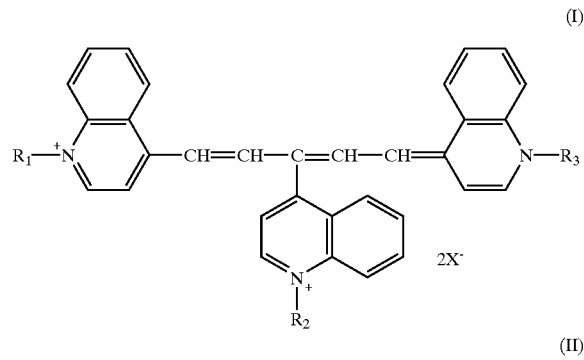

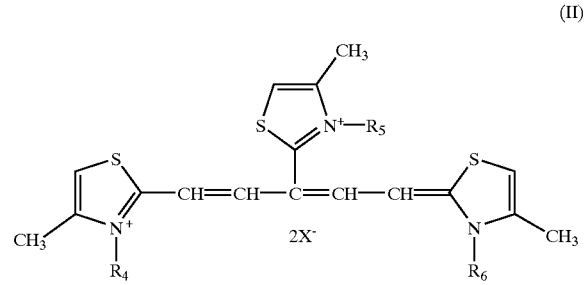

wherein $R_1$, $R_2$ and $R_3$ are the same or different and each represents alkyl group having 1 to 4 carbon atoms, $R_4$, $R_5$ and $R_6$ are the same or different and each represents alkyl group having 5 to 10 carbon atoms, and $X^-$ represents a physiologically acceptable monovalent anion. The present invention also relates to a method for treating or preventing HIV infection diseases, which includes administering the photosensitizing dye. A daily dose of the photosensitizing dye is usually 2 to 100 μg, and preferably 5 to 40 μg, per kg body weight. Administration of the photosensitizing dye to HIV infected subjects leads to improvement or cure of the symptoms of AIDS related complex and increase in CD4-positive lymphocytes, which is effective for the treatment of HIV infection diseases.

18 Claims, No Drawings

ANTI-HIV INFECTION AGENTS AND METHOD FOR TREATING HIV INFECTION

This is a 371 of application PCT/JP98/05925 filed Dec. 24, 1993.

TECHNICAL FIELD

The present invention relates to a medicament useful for treating and preventing HIV infection diseases, and a method for treating or preventing HIV infection diseases. More particularly, the present invention relates to an agent for anti-HIV infection, comprising a photosensitizing dye as an active ingredient. The present invention also relates to a method for treating or preventing HIV infection diseases, which comprises administering the photosensitizing dye.

BACKGROUND ART

Acquired immunodeficiency syndrome (abbreviated as AIDS hereinafter) is now epidemic worldwide. AIDS is caused by infection with human immunodeficiency virus (abbreviated as HIV hereinafter), and therefore, it is rather correct to call it an HIV infection disease. Mere infection with HIV does not cause AIDS, and HIV has an asymptomatic period of several months to several years. After the asymptomatic period, HIV starts to rapidly collapse immune system and causes symptoms such as lymph node enlargement, anorexia, diarrhea, weight loss, fever and languor, which are called AIDS-related complex (abbreviated as ARC hereinafter). With the weakened immune system, microorganisms such as bacteria, viruses, fungi and protozoa, which are harmless in ordinary circumstances, start to affect the body seriously and induce opportunistic infection and the like. These infection diseases are called AIDS, which develop as the immune system weakens. AIDS refers to the condition in a terminal stage of HIV infection diseases, where the immunity is lowered to such a level as to allow development of acquired immunodeficiency syndrome. All the symptoms associated with HIV infection including AIDS are called HIV infection diseases.

Inherently, humans have an immune system as a mechanism for recognizing and eliminating xenobiotics including pathogens. CD4-Positive lymphocytes are well known as the cells that activate immune system. After invading a body, HIV binds to CD4 proteins of CD4-positive lymphocytes and gets into a cell. Since HIV has a reverse transcriptase, it can transcribe its own RNA to DNA and insert the transcribed DNA into the cell's nucleus DNA. Thus, CD4-positive lymphocytes infected with HIV gradually die while producing the virus, thus resulting in a decrease in the cells that control the immune system and destruction of the immune system. Making the situation more difficult in the case of HIV infection diseases, the more the body tries to defend the virus with the immune system, the more actively the virus is produced in the infected cells, which in turn produces an opposite effect of decreased CD4-positive lymphocytes.

With regard to HIV infection diseases, many powerful studies have been carried out to develop clinically effective antiviral agents and vaccines. Examples of medicaments currently under clinical use or clinical trail are a reverse transcriptase inhibitor, absorption inhibitor, dekaryotheca inhibitor, Tat inhibitor, translation inhibitor, protease inhibitor as virus particle synthesis inhibitor, provirus activation inhibitor, HIV protease inhibitor and the like.

Of these medicaments, one of the drugs most frequently used is azidothimidine (abbreviated as AZT hereinafter). AZT was approved as an anti-HIV agent, because its administration significantly lowers mortality. However, AZT has side effects including decrease in neutrophiles, anemia, sleeplessness, nausea and headache, and it only delays the onset of AIDS. While other therapeutic agents have been also tried, they have not proved to be basic therapeutic agents.

Considering the immune system, activation of macrophages is extremely important. For example, when bacteria enter a body, macrophages phagocytize them and become antigen presenting cells while being activated. The information from antigen is transmitted from macrophages to CD4-positive lymphocytes, and further to B-lymphocytes, and the B-lymphocytes produce antibodies. Bacteria bound with antibodies, or immunocomplexes, are phagocytically digested and specifically eliminated speedily by macrophages. At this time, Fc receptors to capture immunocomplexes appear on activated macrophages, and the macrophages show marked increase of phagocytic activity, increased capability of active oxygen production to decompose xenobiotics taken in, reinforced antigen presentation function, and secretion of various cytokines. Ultimately, activated macrophages destroy cancer cells and virus-infected cells in cooperation with NK cell and the like. It is well known that immunity is reinforced by activated macrophages in this way.

DISCLOSURE OF THE INVENTION

As described above, CD4-positive lymphocytes control whole human immune system, such as humoral immunity relating to allergy and bacterial infection, cell-mediated immunity relating to cancer and virus diseases, and activation of macrophage. The onset of AIDS can be explained by the decrease of CD4-positive lymphocytes that command the human immune system. The real cause, nevertheless, is that macrophages are not activated, and therefore, cell-mediated immunity cannot be activated. In lower animals without an immune system, phagocyte cells such as macrophages eliminate xenobiotics. It is considered, therefore, that if macrophages can be activated, the functions of cell-mediated immunity can be improved and virus can be eradicated, even if CD4-positive lymphocytes have decreased.

It is well known that macrophages are activated by macrophage activators, such as interferon-gamma, produced by the above-mentioned CD4-positive lymphocytes. When CD4-positive lymphocytes decrease, however, the macrophage activators also decrease. Thus, an activator that fulfills the decrease should be supplemented. Studies have been done from these viewpoints, which resulted in the completion of the present invention.

It is therefore an object of the present invention to provide a novel medicament useful for treating or preventing HIV infection diseases.

Another object of the present invention is to define the dose of a medicament useful for treating or preventing HIV infection diseases.

A further object of the present invention is to provide a method for treating or preventing HIV infection diseases.

In an attempt to solve the above problems, the present inventors conducted intensive studies and found that, when at least one photosensitizinq dye, selected from the group consisting of the compounds represented by formulae (I) and (II), is administered to an HIV-infected subject, the subject shows improvement or cure of the symptoms of ARC and increase in CD4-positive lymphocytes, thus affording an effective treatment of HIV infection diseases:

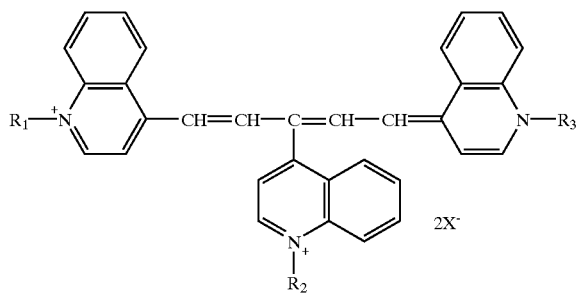

(I)

wherein $R_1$, $R_2$ and $R_3$ may be the same or different and each represents alkyl group having 1 to 4 carbon atoms, and $X^-$ represents a physiologically acceptable monovalent anion, preferably a halogen anion, and more preferably an iodide anion,

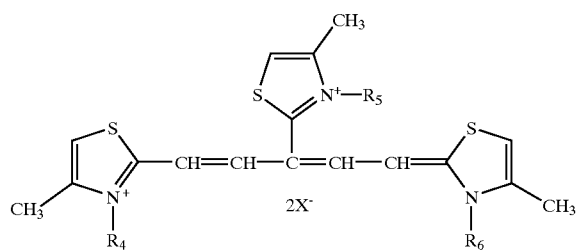

(II)

wherein $R_4$, $R_5$ and $R_6$ may be the same or different and each represents alkyl group having 5 to 10 carbon atoms, preferably linear alkyl group having 7 carbon atoms, and $X^-$ represents a physiologically acceptable monovalent anion, preferably a halogen anion, and more preferably an iodide anion.

Accordingly, the present invention relates to the following.

(1) An anti-HIV infection agent comprising, as an active ingredient, at least one photosensitizing dye selected from the group consisting of the compounds represented by the formula (I) and formula (II) (hereinafter to be also referred to as compound (I) and compound (II), respectively):

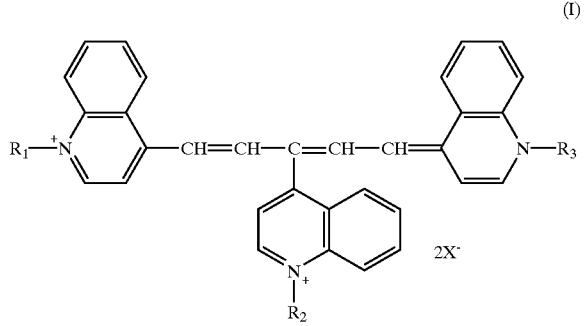

(I)

wherein $R_1$, $R_2$ and $R_3$ may be the same or different and each represents alkyl group having 1 to 4 carbon atoms, and $X^-$ represents a physiologically acceptable monovalent anion, preferably a halogen anion, and more preferably an iodide anion,

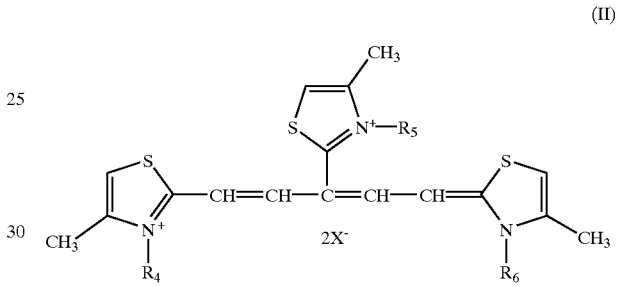

(II)

wherein $R_4$, $R_5$ and $R_6$ may be the same or different and each represents alkyl group having 5 to 10 carbon atoms, preferably linear alkyl group having 7 carbon atoms, and $X^-$ represents a physiologically acceptable monovalent anion, preferably a halogen anion, and more preferably an iodide anion.

(2) The agent for anti-HIV infection of the above (1), wherein a daily dose of at least one photosensitizing dye selected from the group consisting of the compounds (I) and (II) is 2 to 100 μg per kilogram (kg) body weight.

(3) The agent for anti-HIV infection of the above (1), wherein a daily dose of at least one photosensitizing dye selected from the group consisting of the compounds (I) and (II) is 5 to 40 μg per kg body weight.

(4) The agent for anti-HIV infection of any of the above (1) to (3), which is an agent for oral administration.

(5) The agent for anti-HIV infection of the above (1), wherein $X^-$ represents a halogen anion.

(6) The agent for anti-HIV infection of the above (1), wherein $X^-$ represents an iodide anion.

(7) The agent for anti-HIV infection of the above (1), wherein $R_1$, $R_2$ and $R_3$ represent ethyl groups; $R_4$, $R_5$ and $R_6$ represent linear alkyl groups having 7 carbon atoms; and $X^-$ represents an iodide anion.

(8) A method for treating or preventing HIV infection diseases, which comprises administering at least one photosensitizing dye selected from the group consisting of the compounds (I) and (II).

(9) The method of the above (8), wherein a daily dose of at least one photosensitizing dye selected from the group consisting of the compounds (I) and (II) is 2 to 100 μg per kg body weight.

(10) The method of the above (8), wherein a daily dose of at least one photosensitizing dye selected from the group consisting of the compounds (I) and (II) is 5 to 40 μg per kg body weight.

(11) The method of any of the above (8), (9) and (10), wherein the photosensitizing dye is orally administered.

(12) The method of the above (8), wherein $X^-$ represents a halogen anion.

(13) The method of the above (8), wherein $X^-$ represents an iodide anion.

(14) The method of the above (8), wherein $R_1$, $R_2$ and $R_3$ represent ethyl groups; $R_4$, $R_5$ and $R_6$ represent linear alkyl groups having 7 carbon atoms; and $X^-$ represents an iodide anion.

(15) Use of at least one photosensitizing dye selected from the group consisting of the compounds (I) and (II) for the production of an agent for anti-HIV infection.

(16) The use of the above (15), wherein a daily dose of at least one photosensitizing dye selected from the group consisting of the compounds (I) and (II) is 2 to 100 μg per kg body weight.

(17) The use of the above (15), wherein a daily dose of at least one photosensitizing dye selected from the group consisting of the compounds (I) and (II) is 5 to 40 μg per kg body weight.

(18) The use of any of the above (15), (16) and (17), wherein the agent for anti-HIV infection is an agent for oral administration.

(19) The use of the above (15), wherein $X^-$ represents a halogen anion.

(20) The use of the above (15), wherein $X^-$ represents an iodide anion.

(21) The use of the above (15), wherein $R_1$, $R_2$ and $R_3$ represent ethyl groups; $R_4$, $R_5$ and $R_6$ represent linear alkyl groups having 7 carbon atoms; and $X^-$ represents an iodide anion.

(22) A pharmaceutical composition for anti-HIV infection, which comprises at least one photosensitizing dye selected from the group consisting of the compounds (I) and (II), and a pharmaceutically acceptable carrier.

(23) The pharmaceutical composition of the above (22), wherein a daily dose of at least one photosensitizing dye selected from the group consisting of the compounds (I) and (II) is 2 to 100 μg per kg body weight.

(24) The pharmaceutical composition of the above (22), wherein a daily dose of at least one photosensitizing dye selected from the group consisting of the compounds (I) and (II) is 5 to 40 μg per kg body weight.

(25) The pharmaceutical composition of any of the above (22), (23) and (24), which is an agent for oral administration.

(26) The pharmaceutical composition of the above (22), wherein $X^-$ represents a halogen anion.

(27) The pharmaceutical composition of the above (22), wherein $X^-$ represents an iodide anion.

(28) The pharmaceutical composition of the above (22), wherein $R_1$, $R_2$ and $R_3$ represent ethyl groups; $R_4$, $R_5$ and $R_6$ represent linear alkyl groups having 7 carbon atoms; and $X^-$ represents an iodide anion.

(29) A commercial package comprising the pharmaceutical composition of the above (22) and a written matter associated therewith, the written matter stating that the pharmaceutical composition can be or should be used for treating HIV infection diseases.

The embodiments of the present invention are explained in the following.

Alkyl groups having 1 to 4 carbon atoms at $R_1$, $R_2$ and $R_3$ may be straight or branched, and may be, for example, methyl, ethyl, propyl, isopropyl, butyl, isobutyl, sec-butyl or tert-butyl.

Alkyl groups having 5 to 10 carbon atoms at $R_4$, $R_5$ and $R_6$ may be straight or branched, and may be, for example, pentyl, isopentyl, neopentyl, tert-pentyl, hexyl, isohexyl, heptyl, octyl, nonyl or decyl, which are preferably linear alkyl groups having 7 carbon atoms.

The physiologically acceptable monovalent anion at $X^-$ is exemplified by inorganic anion, for example, a halogen anion such as iodide anion, chloride anion, bromide anion and fluoride anion, an alkylsulfuric acid ion wherein alkyl is preferably an alkyl group having 1 to 4 carbon atoms, nitric acid ion, and perchloric acid ion; organic sulfonic acid anion such as p-toluenesulfonic acid ion and benzenesulfonic acid ion; organic carboxylic acid anion such as acetic acid ion, propionic acid ion and benzoic acid ion; and other organic acid anion such as nicotinic acid ion and orotic acid ion; with preference given to halogen anion, and more preference given to iodide anion.

Preferable examples of the active ingredient used for the agent for anti-HIV infection of the present invention include a compound of the formula (I) wherein $R_1$, $R_2$ and $R_3$ are ethyl groups and $X^-$ is an iodide anion, and a compound of the formula (II) wherein $R_4$, $R_5$ and $R_6$ are —$(CH_2)_6CH_3$ and $X^-$ is an iodide anion.

The photosensitizing dyes used as an active ingredient in the present invention can be used alone or in combination of two or more thereof.

The photosensitizing dyes used in the present invention are well-known compounds and can be produced by a method reported by Kendall, J. D. and Majer, J. R. in "*J. Chem. Soc.*", pp. 690 (1948) or a similar method thereto. The anions can be introduced by a known anion exchange method. A compound of the formula (I), wherein $R_1$, $R_2$ and $R_3$ are ethyl groups and $X^-$ is an iodide anion, (abbreviated as active ingredient A hereinafter) is disclosed in JP-A-90025/1991, and a compound of the formula (II), wherein $R_4$, $R_5$ and $R_6$ are —$(CH_2)_6CH_3$ and $X^-$ is an iodide anion, (abbreviated as active ingredient B hereinafter) is disclosed in JP-A-90510/1983. These compounds of the formulae (I) and (II) to be used in the present invention show extremely low toxicity and extremely few side effects and are highly safe, as disclosed in these publications. For example, $LD_{50}$ of the active ingredient B by intraperitoneal administration is 54 mg/kg, and the $LD_{50}$ thereof by oral administration is 1.5 g/kg. The active ingredient A does not cause any side effects such as toxic state even by oral administration at a high concentration of 4 g/kg. When used for agents for oral administration, photosensitizing dyes do not need to be highly purified, and as long as the dyes exert a desired anti-HIV infection activity by oral administration to mammals including humans, no limitation is posed on the production method, properties or purity of the dyes.

The photosensitizing dyes to be used for the anti-HIV infection agent of the present invention are known to have a macrophage activating action as disclosed in, for example, (1) *Cancer Immunology Immunotherapy*, 37, 157–162 (1993) and (2) *J. Photochem. Photobiol. B: Biol.*, 295–306 (1992). It is the finding of the present inventors that an anti-HIV infection agent containing, as an active ingredient, at least one photosensitizing dye, selected from the group consisting of the compounds represented by the formulae (I) and (II), exerts a strikingly superior clinical effect against intractable HIV infection diseases where eradication of virus is difficult.

The present inventors first examined an anti-virus activity of the active ingredients A and B on HIV and found that these compounds had no anti-virus activity to suppress reproduction of HIV. Surprisingly, however, the photosensitizing dye to be used in the present invention exhibited clinical effects of increased CD4-positive lymphocytes of patients infected with HIV and improvement or cure of ARC of patients infected with HIV. This means that the anti-HIV infection agent of the present invention is expected to suppress the onset of AIDS or prolong life after the onset. When an anti-HIV infection agent is administered along with blood transfusion, the therapeutic effect can be increased. This is considered to be related to the need of GC-globulins in serum for the activation of macrophages. The activation of macrophages, which is characteristic of the agent for anti-HIV infection of the present invention, is expressed in the presence of lymphocytes (T- and B-lymphocytes) and GC-globulins. Thus, a synergistic effect can be expected by the agent for anti-HIV infection of the present invention and blood transfusion employed for regular treatment of AIDS.

The agent for anti-HIV infection of the present invention can be administered to mammals including humans, monkeys, cattle, cats and the like.

The agent for anti-HIV infection of the present invention can be used both for oral administration and parenteral administration, such as injection, intrarectal, nasal drop, percutaneous, transmucosal and sublingual administrations. The active ingredient in the present invention can be administered in the form of a conventional pharmaceutical preparation upon mixing with a pharmaceutically acceptable nontoxic carrier in a solid or liquid state, which is suitable for an administration route of oral administration, intrarectal administration, injection administration, nasal drop administration, percutaneous administration, transmucosal administration, sublingual administration and the like. The oral administration of the agent is particularly highly effective, and an adequate amount of the active ingredient, which is generally about 2 to 12 $\mu$g per kg body weight, in tablet or powder may be administered one to several times a day depending on the disease state. The daily dose of the active ingredient, preferably that by oral administration, is generally 2 to 100 $\mu$g per kg body weight, and preferably 5 to 40 $\mu$g per kg body weight. In the case of oral administration, the agent for anti-HIV infection of the present invention is preferably held and dissolved in the mouth on an empty stomach. Although the effective dose varies depending on individual difference, the dose can be increased or decreased using, as an index, vitality, appetite, sleep, urination, biorhythm, relief from constipation, and manifestation of other useful subjective responses of patients under medication, because the agent for anti-HIV infection of the present invention shows extremely low toxicity, extremely few side effects and superior safety. The agent for anti-HIV infection of the present invention is also advantageous in that it can control biorhythm of body and affords self-judgment of adequate dose based on subjective symptoms.

Examples of the dosage form of the agent for anti-HIV infection of the present invention include oral agents such as tablets, pills, powders, granules, capsules, troches and syrups, injections, suppositories, collunariums, preparations for percutaneous administration such as ointments, creams and plasters, preparations for transmucosal administration, sublinguals, atomizers, inhalants and the like.

Examples of the pharmaceutically acceptable carriers include excipients such as lactose, corn starch, sucrose, glucose, sorbitol, mannitol, maltose, trehalose, crystalline cellulose, carboxymethylcellulose, calcium carboxymethylcellulose, sodium hydrogencarbonate and dextrin; binders such as methylcellulose, gum arabic, tragacanth gum, gelatin, hydroxypropylcellulose, hydroxypropylmethylcellulose, polyvinylpyrrolidone, pullulan and sucrose fatty acid ester; thickening agents such as sodium carboxymethylcellulose, calcium calboxymethylcellulose, polyvinylpyrrolidone, hydroxypropylcellulose, hydroxypropylmethylcellulose and methylcellulose; lubricants such as magnesium stearate, calcium stearate, talc and light anhydrous silicic acid; base for suppository such as polyethylene glycol and cacao butter; and inorganic or organic solvents such as distilled water, distilled water for injection, sterile purified water, physiological saline, plant oils (olive oil, sesami oil, soybean oil, corn oil and peanut oil), glycerin, ethanol and propylene glycol. Furthermore, additives such as preservatives (e.g., sodium benzoate, benzalkonium chloride, benzethonium chloride, methyl p-hydroxybenzoate, ethyl p-hydroxybenzoate, propyl p-hydroxybenzoate, butyl p-hydroxybenzoate, sorbic acid and potassium sorbate); emulsifiers (e.g., glyceryl monostearate); and pH adjusting agents including buffers (e.g., hydrochloric acid, citric acid, acetic acid, tartaric acid, sodium hydrogencarbonate, sodium hydroxide and sodium carbonate) can be added to the pharmaceutical preparation of the present invention.

The agent for anti-HIV infection of the present invention can be used in combination with other medicaments. Examples of such medicaments include antiviral agents, antibiotics, analgesic antipyretics, mucous membrane preventive agents, immunostimulants, vitamins, skin protective agents and the like.

The antiviral agents that can be used in combination with the agent for anti-HIV infection of the present invention are not particularly limited so far as they are anti-HIV agents usable for the treatment of HIV infection diseases. Preferable examples of the antiviral agents are nucleoside derivatives such as AZT, dideoxyinosine (ddI), dideoxycytidine (ddC), lamivudine (3TC) and stavudine (d4T); protease inhibitors such as indinavir (IDV), saquinavir, ritonavir (RTV) and nelfinavir; and interferons such as interferon-$\alpha$, interferon-$\beta$ and interferon-$\gamma$. One or more of these antiviral agents can be used in combination with the agent for anti-HIV infection of the present invention.

Examples of the antibiotics usable in combination with the agent for anti-HIV infection of the present invention include antibacterial agents and antifungal agents including those for andidasis, Pneumocystis carinii pneumonia and the like.

In the present invention, by the "HIV infection diseases" is meant the condition of infection with HIV, including AIDS, symptomatic or asymptomatic HIV infection diseases such as ARC, and the like.

In the present invention, by the "agent for anti-HIV infection" is meant medicaments for prevention and/or treatment of HIV infection diseases. The "treatment" includes that aiming at improvement, alleviation and cure of symptoms. The "treatment of HIV infection diseases" includes that aiming at improvement, alleviation and cure of symptoms caused by HIV infection, and prevention and delaying of the onset of AIDS. Concrete examples include treatments aiming at increasing or suppressing the decrease in CD4-positive lymphocytes; increasing or suppressing the decrease in NK cell activity; prevention, improvement, alleviation or cure of ARC; prevention or delay of the onset of AIDS; prevention, improvement, alleviation or cure of opportunistic infection; and improvement, alleviation or cure of the symptoms of AIDS. The symptoms of ARC include lymph node enlargement, anorexia, diarrhea, weight loss, fever, languor, eruption, bronchial asthma and the like.

The therapeutic effect achieved by the agent for anti-HIV infection of the present invention can be confirmed by improvement or cure of the symptoms of ARC, particularly by weight gain or suppression of weight loss of patients infected with HIV or by measuring an increase or suppression of decrease in CD4-positive lymphocytes or increase/decrease of cellular immune activity (NK cell activity, ratio of T/B) of patients infected with HIV.

EXAMPLES

The present invention is described in more detail by the following preparation examples, experimental examples and clinical experimental examples according to the present invention.

Preparation Example

Formulation 1
Tablet

| Ingredient | mg/tablet |
| --- | --- |
| Photosensitizing dye | 0.1 |
| Sodium hydrogencarbonate | 67.0 |
| Gum arabic | 0.8 |
| Talc | 2.1 |
| Total | 70 |

Two types of tablets were prepared in a conventional manner using the active ingredient A or B as a photosensitizing dye in the above formulation.

Formulation 2
Troche

| Ingredient | mg/tablet |
| --- | --- |
| Active ingredient B | 0.1 |
| Lactose | 79.9 |
| Corn starch | 62.5 |
| Sucrose fatty acid ester | 7.5 |
| Total | 150 |

A troche of the above formulation was prepared in a conventional manner.

Formulation 3
Powder for Injection

| Ingredient | mg/ampoule |
| --- | --- |
| photosensitizing dye | 0.2 |
| Glucose | 49.8 |
| Total | 50 |

Two types of powders for injection were prepared in a conventional manner using the active ingredient A or B as a photosensitizing dye in the above formulation.

Formulation 4
Troche

| Ingredient | mg/tablet |
| --- | --- |
| Active ingredient A | 0.1 |
| Lactose | 79.9 |
| Sodium hydrogencarbonate | 62.5 |
| Sucrose fatty acid ester | 7.5 |
| Total | 150 |

A troche of the above formulation was prepared in a conventional manner.

Experimental Example 1

To examine the effect on HIV infected cell, MT-4 cells (number of cells at the start of culture $1 \times 10^4$/well), that underwent anti-HIV assay, were infected with an HIV (HTLV-IIIB, 200 $CCID_{50}$/well), cultured at 37° C. for 4 days, and determined for the inhibitory effect on HIV replication, according to the method by Pauels, R. et al., in *J. Virol. Methods*, 16, 171–185 (1987). Suramin was used as a control. Table 1 shows the results.

TABLE 1

| [Compound] | [Concentration ($\mu M$)] | [Inhibition (%) of HIV replication] |
| --- | --- | --- |
| Active ingredient B | 500 | 2 |
| | 100 | 1 |
| | 20 | 2 |
| Active ingredient A | 500 | 1 |
| | 100 | 2 |
| | 20 | 1 |
| Suramin | 100 | 100 |
| | 20 | 100 |
| | 4 | 10 |
| | 0.8 | 2 |

As is evident from the above results, the active ingredients A and B did not suppress the replication of HIV at the tested concentrations.

The clinical experiments using the agent for anti-HIV infection of the present invention are explained in the following. The clinical experiments described below were conducted in Thailand without informing the patients of the compound names, chemical structures, etc. of the photosensitizing dyes used as the active ingredient.

Clinical Experiment 1

The agent for anti-HIV infection of the present invention was administered to a patient (male, 39 years old) suffering from ARC. He had been diagnosed with HIV infection five years before and received administration of AZT/ddI/RTV for 14 months. This patient showed a CD4-positive lymphocyte (abbreviated as CD4 hereinafter) count of 121/mm$^3$ and the body weight of 55.6 kg before administration of the agent for anti-HIV infection of the present invention.

This patient, after administration of the agent for anti-HIV infection of the preset invention of formulation 1 containing the active ingredient A (daily dose of active ingredient A 500 µg) for 8 weeks, showed an increase in the CD4 count to 181/mm$^3$ and in the body weight to 56.9 kg. He also showed increased appetite and increased pectoral muscle.

Subsequently, he was given the agent for anti-HIV infection of the preset invention of formulation 1 containing the active ingredient A (daily dose of active ingredient A 1000 µg) for 16 weeks and showed an increase in the CD4 count to 192/mm$^3$ and in the body weight to 57.1 kg. His bronchial asthma, a symptom of ARC, was also cured.

Clinical Experiment 2

Seven patients suffering from ARC or AIDS were given the agent for anti-HIV infection of the present invention of formulation 1 containing the active ingredient A. Their medical history before treatment was as follows:

Patient No. 1 (male, 35 years old) had been diagnosed with HIV infection 2 years and 4 months before and received administration of AZT/3TC/IDV for 7 months. He showed a CD4 count of 165/mm$^3$ and the body weight of 76.3 kg before administration of the agent for anti-HIV infection of the present invention.

Patient No. 2 (male, 42 years old) had been diagnosed with HIV infection 3 years and 5 months before and started to receive administration of AZT/3TC/IDV at once. He showed a CD4 count of 92/mm$^3$ and the body weight of 76.2 kg before the administration of the agent for anti-HIV infection of the present invention.

Patient No. 3 (male, 32 years old) had been diagnosed with HIV infection 1 year and 9 months before and already developed AIDS. He had received administration of AZT/3TC for 21 weeks, and showed a CD4 count of 180/mm$^3$ and the body weight of 53.8 kg before the administration of the agent for anti-HIV infection of the present invention.

Patient No. 4 (male, 54 years old) had been diagnosed with HIV infection 7 years and 2 months before and received administration of AZT/ddI for 2 years and 10 months and additionally of RTV for 1 year and 11 months. This patient showed an increase in the CD4 count in the beginning of administration of the anti-HIV agent, but thereafter showed gradual decrease in the CD4 count to 222/mm$^3$. The body weight was 76 kg before the administration of the agent for anti-HIV infection of the present invention.

Patient No. 5 (male, 32 years old) had been diagnosed with HIV infection 7 years before and showed a CD4 count of 317/mm$^3$ before the administration of the agent for anti-HIV infection of the present invention.

Patient No. 6 (female, 33 years old) had been diagnosed with HIV infection 4 years and 2 months before and received administration of AZT/ddI for 1 year and 8 months. She showed a CD4 count of 353/mm$^3$ and the body weight of 45.6 kg before the administration of the agent for anti-HIV infection of the present invention.

Patient No. 7 (male, 32 years old) had been diagnosed with HIV infection 3 years and 4 months before and received administration of AZT/ddI, which had been changed to IDV/d4T/3TC 9 months before. He showed a CD4 count of 254/mm$^3$ and the body weight of 58.2 kg before the administration of the agent for anti-HIV infection of the present invention.

Each patient received the administration of the agent for anti-HIV infection of the preset invention of formulation 1 containing the active ingredient A (daily dose of active ingredient A 500 µg) for 8 weeks, and most of the patients showed an increase in the CD4 count and in the body weight. Along therewith, their appetite increased, rash, one of the symptoms of ARC, decreased, hemorrhoid was cured, and insomnia was ameliorated. Table 2 shows the results.

TABLE 2

| | | Administration of active ingredient A for 8 weeks (500 µg/day) | | | |
|---|---|---|---|---|---|
| Patient No. | Gender | Change of Body weight | Change of CD4 | Improvement (Symptoms of ARC etc.) | Side effects |
| 1 | Male | 76.3 kg→79.4 kg | 165→206 | Cure of hemorrhoids | None |
| 2 | Male | 76.2 kg→76 kg | 92→102 | Decrease of rash | None |
| 3 | Male | 53.8 kg→53.3 kg | 180→143 | | None |
| 4 | Male | 76 kg→73.4 kg | 222→270 | Increased appetite | None |
| 5 | Male | 57.1 kg#→57.6 kg | 317→353 | Increased appetite | None |
| 6 | Female | 45.6 kg→46.4 kg | 353→358 | Amelioration of insomnia | None |
| 7 | Male | 58.2 kg→59.1 kg | 254→330 | Increased appetite | None |

"#": body weight at week 4 of administration of active ingredient A.

As is evident from these results, the agent for anti-HIV infection of the present invention shows a remarkable effect. The agents of formulations 2 to 4 also showed similar effects.

Industrial Applicability

It is said that 6% of HIV infected patients develop AIDS every year. The patients who developed AIDS have extremely weakened cellular immunity, and suffer from complications of opportunistic infections, such as Pneumocystis carinii pneumonia, Kaposi sarcoma and brain disorder (dementia), which is ultimately followed by death. In the treatment of AIDS patients and asymptomatic HIV-infected patients, the agent for anti-HIV infection of the present invention can achieve several effects. one of them is an increase in CD4-positve lymphocytes. Another is cure of AIDS-related complex (ARC). A further effect is increase of appetite and weight gain. Based on these effects, the agent can prevent or delay the onset of AIDS and prolong life of HIV-infected patients. While the treatment of HIV infection diseases inevitably takes a long time, the agent for anti-HIV infection of the present invention is extremely useful for the treatment of HIV infection diseases, because it shows extremely low toxicity, extremely few side effects and superior safety.

It is considered that the agent for anti-hiv infection of the present invention activates macrophages, thereby to improve biological function of eliminating xenobiotics, increase CD4-positve lymphocyte count, and cure arc.

What is claimed is:

1. A method for treating or preventing HIV infection diseases, which comprises administering at least one photosensitizing dye selected from the group consisting of compounds represented by the formulae (I) and (II):

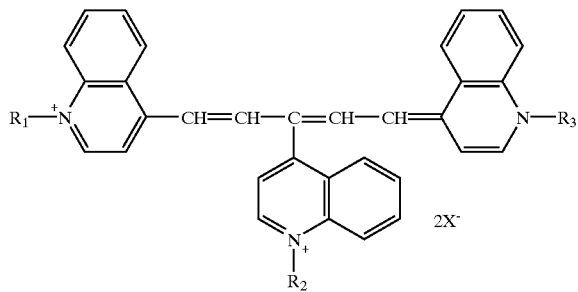

(I)

wherein $R_1$, $R_2$ and $R_3$ are the same or different and each represents alkyl group having 1 to 4 carbon atoms, and $X^-$ represents a physiologically acceptable monovalent anion,

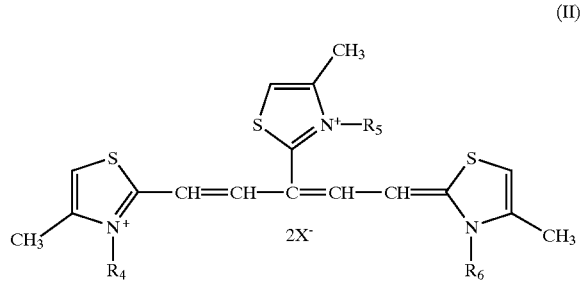

(II)

wherein $R_4$, $R_5$ and $R_6$ are the same or different and each represents alkyl group having 5 to 10 carbon atoms, and $X^-$ represents a physiologically acceptable monovalent anion.

2. The method of claim 1, wherein said photosensitizing dye is administered in a daily dose of 2 to 100 µg per kg body weight.

3. method of claim 1, wherein said photosensitizing dye is administered in a daily dose of 5 to 40 µg per kg body weight.

4. The method of claim 1, wherein said photosensitizing dye is orally administered.

5. The method of claim 1, wherein $X^-$ represents a halogen anion.

6. The method of claim 1, wherein $X^-$ represents an iodide anion.

7. The method of claim 1, wherein $R_1$, $R_2$ and $R_3$ represent ethyl groups; $R_4$, $R_5$ and $R_6$ represent linear alkyl groups having 7 carbon atoms; and $X^-$ represents an iodide anion.

8. A pharmaceutical composition comprising an anti-HIV infection effective amount of at least one photosensitizing dye represented by the formula II:

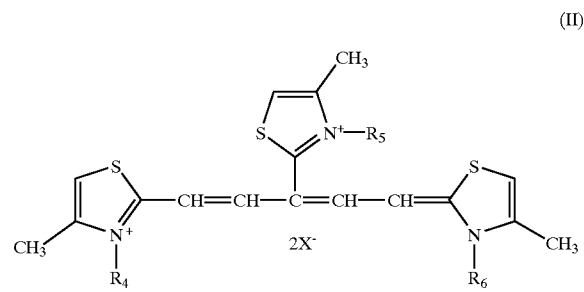

(II)

wherein $R_4$, $R_5$ and $R_6$ are the same or different and each represents alkyl group having 5 to 10 carbon atoms, and $X^-$ represents a physiologically acceptable monovalent anion, optionally at least one photosensitizing dye represented by the formula (I):

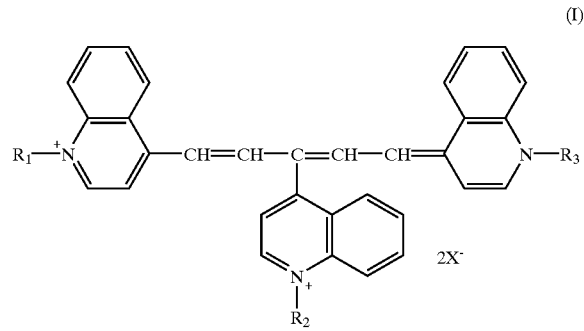

(I)

wherein $R_1$, $R_2$ and $R_3$ are the same or different and each represents alkyl group having 1 to 4 carbon atoms, and $X^-$ represents a physiologically acceptable monovalent anion, and a pharmaceutically acceptable carrier.

9. The pharmaceutical composition of claim 8, wherein the pharmaceutical composition comprises a daily dose of said photosensitizing dye of 2 to 100 µg per kg body weight.

10. The pharmaceutical composition of claim 8, wherein the pharmaceutical composition comprises a daily dose of said photosensitizing dye of 5 to 40 µg per kg body weight.

11. The pharmaceutical composition of claim 8, which is in a form for oral administration.

12. The pharmaceutical composition of claim 8, wherein $X^-$ represents a halogen anion.

13. The pharmaceutical composition of claim 8, wherein $X^-$ represents an iodide anion.

14. The pharmaceutical composition of claim 8, wherein $R_1$, $R_2$ and $R_3$ represent ethyl groups; $R_4$, $R_5$ and $R_6$ represent linear alkyl groups having 7 carbon atoms; and $X^-$ represents an iodide anion.

15. method of claim 2, wherein said photosensitizing dye is orally administered.

16. The method of claim 3, wherein said photosensitizing dye is orally administered.

17. The pharmaceutical composition of claim 9, which is in a form for oral administration.

18. The pharmaceutical composition of claim 10, which is in a form for oral administration.

* * * * *

UNITED STATES PATENT AND TRADEMARK OFFICE
CERTIFICATE OF CORRECTION

PATENT NO. : 6,455,555 B1
DATED : September 24, 2002
INVENTOR(S) : Nakagawa et al.

It is certified that error appears in the above-identified patent and that said Letters Patent is hereby corrected as shown below:

Column 13,
Line 55, "method" should read -- The method --.

Column 14,
Line 58, "method" should read -- The method --.

Signed and Sealed this

Fourth Day of March, 2003

JAMES E. ROGAN
*Director of the United States Patent and Trademark Office*